United States Patent
Dean et al.

(10) Patent No.: US 6,245,717 B1
(45) Date of Patent: Jun. 12, 2001

(54) SUPPRESSION OF AUXIN IN HIGHER PLANTS

(76) Inventors: Frank Dean, 25414 Sugar Valley, Spring, TX (US) 77273; Tim Loy, 30518 Woodhue Ct., Spring, TX (US) 77386; T. Regina Vamvakias, 615 Pike Edge Dr., Spring, TX (US) 77380

( * ) Notice: Subject to any disclaimer, the term of this patent is extended or adjusted under 35 U.S.C. 154(b) by 13 days.

(21) Appl. No.: 09/610,252

(22) Filed: Jul. 5, 2000

Related U.S. Application Data

(60) Provisional application No. 60/142,372, filed on Jul. 6, 1999.

(51) Int. Cl.[7] ........................................ A01N 37/10
(52) U.S. Cl. ................................................ 504/321
(58) Field of Search ............................... 504/321

(56) References Cited

PUBLICATIONS

Davies, Plant Harmones, Physiology, Biochemistry, Molecular Biology, Kewler Academic Press, pp. 4–5,235, 1988.*

Davranov et al, Effect of organic acids on the activity of malate dehydrogenase of cotton seeds, Inst. Khim Prir. Soedin, vol. 2, pp. 234–6, 1972.*

* cited by examiner

*Primary Examiner*—S. Mark Clardy
*Assistant Examiner*—Alton Pryor

(57) ABSTRACT

The present invention is directed to methods for control of auxin production, expression, and/or auxin movement in higher plants. In these methods 4-phenylbutyric acid is applied to a plant, seed, or surrounding soil.

3 Claims, No Drawings

SUPPRESSION OF AUXIN IN HIGHER PLANTS

This patent application is based in part on U.S. Provisional patent application No. 60/142,372, filed Jul. 6, 1999.

BACKGROUND OF THE INVENTION

Bursts of vegetative growth often compete with the source-sink relationships between the vegetative parts and the reproductive organs of higher plants. Those skilled in the art have often turned to Gibberellic acid transport or synthesis inhibition to control a flush of growth, i.e., plant height. While those measures are successful in controlling plant height they do not normally contribute to yield.

Auxins are known to regulate many of the physiological events in a plants life cycle. Some of these regulated events are phototropism, gravitropism, apical dominance, leaf and fruit abscission, and root initiation.

Plant shoots display positive phototropism. When plants are illuminated from one direction the shoot grows in that direction. Auxin is synthesized at the tip and translocated down along the shady side of the shoot. Auxin stimulates elongation of the cells on the shady side causing the shoot to bend toward the light.

Gravitropism is a plant growth response to gravity. Plant shoots exhibit negative gravitropism. When a plant is laid on its side a plant shoot will grow up. The opposite is true of roots. Roots show positive gravitropism because they grow down. When a root is placed on its side amyloplasts (organelles containing starch grains) settle to the bottom of cells in the root tip. Auxin sent down from the shoot arrives in the central tissues of the root tip and is then translocated back along the under side of the root. This inhibits root cell elongation on the lower side of the root. The cells at the top surface of the root elongate causing the root to grow down.

Growth of the shoot apex (terminal shoot) usually inhibits the development of the lateral buds on the stem beneath. This phenomenon is called apical dominance. If the terminal shoot of a plant is pruned the inhibition is lifted and lateral buds begin growth. The release from apical dominance enables lateral branches to develop and the plant becomes bushier. Apical dominance results from the downward transport of auxin produced in the apical meristem. In fact, if the apical meristem is removed and indole-3-acetic acid is applied to the plant's pruned apex inhibition of the lateral buds is maintained.

Auxin plays a role in the abscission of leaves and fruits. Young leaves and fruits produce auxin and they remain attached to the stem. When the level of auxin declines an abscission layer forms at the base of the petiole. Soon the petiole or fruit stalk breaks free. Fruit growers often apply auxin sprays to cut down the loss of fruit from premature dropping.

Auxins stimulate the formation of adventitious roots in many plant species. Adventitious roots grow from stems or leaves rather than from the regular root system of the plant. Horticulturists may propagate desirable plants by cutting pieces of stem and placing them base down in moist soil. Eventually adventitious roots grow out at the base of the cutting. The process can often be hastened by treating the cuttings with a solution or powder containing a natural or synthetic auxin.

SUMMARY OF THE INVENTION

Plant hormones are currently used for initiating growth, controlling growth, to promoting flowering, thinning flowers, providing drought protection, ripening fruit and various other responses. The present invention is directed to methods for control of auxin, a class of growth regulators. More specifically the present invention is directed to controlling the production and/or movement of auxin in higher plants. Higher plants display the influence of auxins. In the methods of the invention 4-phenylbutyric acid is applied to a plant, seed, or surrounding soil. The treatment can be applied in solution with an adequate carrier or as a dry material.

DETAILED DESCRIPTION OF THE PREFERRED EMBODIMENT

The present invention is directed toward methods for control of auxin—a class of growth regulators; more specifically, the present invention is directed to methods for suppressing of the production and/or movement of auxin in higher plants. Higher plants display the influence of auxins. This influence prohibits the branching at axil buds. When the ail buds are released from this hormonal dominance branching occurs. Each axil branch has the potential to produce it's own flowers, fruiting points, and seed. In multiple fruiting crops the number of fruiting points on a plant dictate the commercial yield.

Because so much of a plant's physiology is regulated by the auxin hormones, and because prior art, methods to limit, or effect, the growth regulating abilities of the auxins involved pruning or some other mechanical means, there is a genuine desire for an improved method of eliciting a pruning response.

The method of the invention employs the use of 4-penylbutyric acid, or its salts, for application to plants to release the plant from auxin influence. In multiple fruiting plants, the application of an antiauxin will promote branching These branches will in turn produce flowers, fruiting points and seed.

The relative auxin concentration ratio to other plant hormones that control these biological events can also be influenced with the application of an auxin inhibitor blended with natural or synthetic plant growth regulators.

EXAMPLES

Example 1

In a preliminary trial four sets of 8 soybean plants were grown to 8 to 10 nodes. Control plants were untreated. A second set was pruned. The third and forth sets were treated with 7.0e-3M and 0.024M concentrations of 4-phenylbutyric acid respectively. The compound was dissolved in ethyl alcohol, blended with a surfactant, and diluted in water. While the control plants maintained their apical dominance the pruned plants did show branching at the axil nodes. Both sets of the plants treated with the 4-phenylbutyric acid compound also had branching at the axils as if they had been pruned. The lowest effective or optimum dose is still to be determined.

Example 2

A soybean germination trial was set up to determine the effects of 4-phenylbutyric acid on seed germination. Ten seed imbibed in water were set as controls. A second set of ten seed was imbibed in water and 4-phenylbutyric acid. The treated seed radicals emerged simultaneously with the control set and the gravitropic response was apparently affected. The embryonic radicals had no propensity to grow in a downward direction, in fact, some radicals grew in an upward direction.

Example 3

Jalapeno pepper plants were transplanted into one-gallon pots into a soil medium. On the day of transplant the plants were foliar sprayed with 4-phenylbutyric acid at one gram per liter with a nonionic surfactant added. Results of the treatment follow.

| FIRST FRUIT HARVEST | | | | | | |
|---|---|---|---|---|---|---|
| | Number of plants | Number of fruit | Total weight g of fruit | avg. fruit weight g/fruit | number fruit per plant | avg. fruit weight g per plant | % change |
| Control | 6 | 50 | 330 | 6.6 | 8.3 | 55.0 | 0.0% |
| Treated | 7 | 56 | 404 | 7.2 | 8.0 | 57.7 | 4.9% |

| SECOND FRUIT HARVEST | | | | | | |
|---|---|---|---|---|---|---|
| | Number of plants | Number of fruit | Total weight g of fruit | avg. fruit weight g/fruit | number fruit per plant | avg. fruit weight g per plant | % change |
| Control | 6 | 54 | 608 | 11.3 | 9.0 | 101.3 | 0.0% |
| Treated | 7 | 109 | 1388 | 12.7 | 15.6 | 198.3 | 95.7% |

Because the transplants were flowering when they were treated the effects of the treatment were not seen until the second harvest. The increased number of fruit came from the branching of the axil buds. Those branches produced flowers and fruit for the second harvest. The branches were expressed at each node above the cotyledons.

Example 4

A growth chamber had the following settings:

Twenty four hours of daylight

Temperature set at 15° C. for four hours and twenty hours set at 20° C. 60% humidity Five soybean seeds were planted in a soil medium in one-gallon pots. One set of pots were watered with deionized water while another set was watered with the addition of 4-phenylbutyric acid at 0.1 g per liter with a surfactant added. Essentially all the seed germinated. The treated pots continued to thrive after five weeks, however, the plants in the untreated soil died. The plants first showed the browning of leaves followed by leaf abscission. The trial was terminated and there were no visual differences in the root system physiology. It is suspected the treatment had affected the allopathic response somehow.

Example 5

A second soybean germination trial was set up to determine the effects of 4-phenylbutyric acid on seed germination. Ten seed imbibed in water were set as controls. A second set of ten seed was imbibed in water and 4-phenylbutyric acid. Still another set were imbibed in water with sodium formate buffer. All of treated all seed radicals emerged simultaneously with the control set, and, the gravitropic response was apparently affected. However, the addition of formate buffer did affect the emergence somewhat.; there was a uniformity in the growth of the radicals in that treatment. Again the embryonic radicals had no propensity to grow in a downward direction.

This patent application is intended to cover the use of 4-phenylbutyric acid and it's salts for use in agriculture. It should be understood that it is the biological events and biochemistry of living organisms that are acted upon. It may be that these compounds or techniques will be extended to organisms outside the plant kingdom.

Let it also be understood that it is the molecular structure of the compound that initiates or inhibits certain biological events. It is understood that the 4-phenylbutyric acid may be changed via chemical reaction as an addition, subtraction, oxidation, reduction, or substitution of the core molecule. Whilst an addition, subtraction, or change in functionality may alter the biological response this applicant envisions those types of modifications. It is assumed any structural change may produce a herbicide, pesticide, defoliant or unlisted growth regulating response when applied to a higher plant.

The preferred compositions of the invention may include one or more surfactants, which have been found to aid in preparation of other compositions of this invention and may assist in penetration of the active components. Many types of surfactants can aid in the preparation of the composition including anionic, cationic, and amphoteric surfactants. Nonionic surfactants include: Polyoxy propylene polyoxyethylene block copolymers, Alkyl aryl ethoxylates and or alkoxylates, Fatty acid ethoxylates and or alkoxylates, Fatty alcohol ethoxylates and or alkoxylates, Fatty amine ethoxylates and or alkoxylates, Vegetable or seed oil ethoxylates and or alkoxylates, Sorbitan fatty acid ester ethoxylates and or alkoxylates, and Alkyl polysaccharides.

The composition of the invention may be formulated in a wide range of forms known in the art. The composition may, for example, be in the form of a concentrate to be diluted prior to application or it may be in the form of a granule, powder or liquid with a suitable solid or liquid carrier. For example, the composition of this invention may be in the form of an emulsion, or dispersion in water, and, may comprise solvents or agricultural chemicals. Alternatively formulations of this invention may be adapted to form an emulsion when diluted with water prior to use.

Higher concentrations of growth regulating compound may be present in the composition when, for example, in a form suitable for use as an ultra low volume spray, which may merely contain the active agents.

Often those skilled in the art find synergistic combinations when blending or admixing growth regulating compounds found during delivery of the growth regulating compounds. Frequently the active component is not acting synergistically but merely in combination with compounds known for producing a response.

Discussion of Possible Components for Admixes:

For their practical application, the compounds according to the invention are rarely used on their own. Instead they generally form part of formulations which, as a rule, contain a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (e.g, clays, natural or synthetic silicates, resins, waxes, solid fertilizers) or fluid (water, alcohols, ketones, petroleum fractions, chlorinated hydrocarbons, liquefied gases, liquid fertilizers).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain the active material, and they normally contain, in addition to a solid support, a wetting agent, a dispersant and, when necessary, one or more stabilizers and/or other additives, such as penetration agents, adhesives or anti-lumping agents, colorants etc.

Aqueous dispersions and emulsions, such as: for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thioxtropic agents, stabilizers or sequestrants, as well as other active materials. A modest list of possible formulation components follows.

A Carbon Skeleton/Energy (CSE) Component:

The supposed function of this component is to supply carbon skeleton for synthesis of proteins and other molecules or to supply energy for metabolism. Water-soluble carbohydrates such as sucrose, fructose, glucose and other di- and monosaccharides are suitable, commonly in the form of molasses or other byproducts of food manufacture. Commercially available lignosulfonates, discussed below under the heading "Complexing Agents," are also suitable as a CSE source inasmuch as they commonly contain sugars.

CSE Components:

sugar—mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate sugar alcohol—adonitol, galactitol, glucitol, maltitol, mannitol, mannitol-p, ribitol, sorbitol, sorbitol-p, xylitol organic acids—glucuronic acid, a-ketoglutaric acid, galactonic acid, glucaric acid, gluconic acid, pyruvic acid, polygalacturonic acid, saccharic acid, citric acid, succinic acid, malic acid, oxaloacetic acid, aspartic acid, phosphoglyceric acid, fulvic acid, ulmic acid, humic acid, gultamic acid. nucleotides and bases--adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH (2) The Macronutrient Component:

The macronutrients are essential to nutrition and growth.. The most important macronutrients are N, P and K.. Some Nitrogen compounds are: ammonium nitrate, monoammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium Cyanamid, sodium nitrate, urea, urea-formaldehyde, urea-ammonium nitrate solution, nitrate of soda potash, potassium nitrate, amino acids, proteins, nucleic acids.

Phosphate sources include: superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates phosphorous acid salts and Phosphonic acid derivatives.

The potassium ion can be found in: potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate and the like.

Calcium sources include: calcium ammonium nitrate, calcium nitrate, calcium Cyanamid, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate and the like.

Magnesium can be found in: magnesium oxide, dolomite, magnesium acetate, magnesium bensoate, magnesium bisulfate, magnesium borate, magnesium chloride, magnesium citrate, magnesium nitrate, magnesium phosphate, magnesium salicylate, magnesium sulfate. Sulfur containing compounds include: ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine and elemental sulfur.

(3) Micronutrient Component:

The most important micronutrients are Zn, Fe, Cu, Mn, B, Co, and Mo.

(4) Vitamin/Cofactor Component:

The most important are folic acid, biotin, pantothenic acid, nicotinic acid, riboflavin and thiamine. Thiamine-- thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract Riboflavin—riboflavin acetyl phosphate, flavin adenine dinucleotide, flavin adenine mononucleotide, riboflavin phosphate, yeast, yeast extract. Nicotinic acid--nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile. Pyridoxine—pyridoxal phosphate, yeast, yeast extract Folic acid—yeast, yeast extract, folinic acid. Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine. Pantothenic acid— yeast, yeast extract, coenzyme A,Cyanocobalamin—yeast, yeast extract. Phosphatidylcholine-soybean oil, eggs bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh, B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl, L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl) DL-a-PTCh di-O-hexadecyl (dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohexanoyl)-g-palmitoyl, L-a-PTCh, B-oleoyl-g-O-palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl. Inositol—inositol monophosphate, inositol macinate, myo-inositol, epi-inositol, myo-inositol 2,2'anhydro-2-c-hydroxymethyl (2-c-methylene-myoinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol PABA--m-aminobenzoic acid, 0-aminobenzoic acid, p-aminobenzoic acid butyl ester, PABA ethyl ester, 3-ABA ethyl ester.

(5) Complexing Agents:

The function of this component, aside from its proposed use as a Carbon skeleton agent, is to solubilize other components of the composition which otherwise may precipitate and become assailable or may immobilize minerals in the soil which might otherwise be unavailable to flora and fauna. Complexing agents such as citric acid, humic acids, lignosulfonate, etc. serve to tie up ions such as iron and prevent them from forming precipitates. In some cases this complexing is by way of chelation. These agents may form complexes with the following compounds: Citric acid; Ca, K, Na and ammonium lignosulfonates, fulvic acid, ulmic acid, humic acid, Katy-J, EDTA, EDDA, EDDHA, HEDTA, CDTA, PTPA, NTA, MEA IDS and 4-phenylbutyric acid. Al and its salts, Zn--zinc oxide, zinc acetate, zinc bensoate, zinc chloride, zinc citrate, zinc nitrate, zinc saticylate, ziram Fe--ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate. Mn--manganese acetate, manganese chloride, manganese nitrate, manganese phosphate Cu—cupric acetate, cupric butyrate, cupric chlorate, cupric chloride, cupric citrate, cupric gluconate, cupric glycinate, cupric nitrate, cupric salicylate, cuprous acetate, cuprous chloride. B—calcium borate, potassium borohydride, borax, boron trioxide, potassium borotartrate, potassium tetraborate, sodium borate, sodium borohydride, sodium tetraborate and boric acid. Mo—molybdic acid, calcium molybdate, potassium molybdate, sodium molybdate. Co—cobaltic acetate, cobaltous acetate, cobaltous chloride, cobaltous, cobaltous oxalate, cobaltous potassium sulfate, cobaltous sulfate.

GrowthRegulators:

Seaweed extract—kelp extract, kinetin, Kinetin riboside, benzyladenine, zeatin riboside, zeatin, extract of corn cockle, isopentenyl adenine, dihydrozeatin, indoleacetic acid, phenylacetic acid, IBA, indole ethanol, indole acetaldehyde, indoleacetonitrile, indole derivitives, gibberellins (e.g. GA1, GA2, GA3, GA4, GA7, GA38 etc.) polyamines, monoethanolamine, allopurinol, GA inhibitors, ethylene inducing compounds, ethylene biosynthesis inhibitors, GABA, anticytokinins and antiauxins, ABA inducers and inhibitors, and other known growth regulators Gum Components:

Xanthan gum—guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth.

Microbialstats, Proprionic acid, benzoic acid, sorbic acid and amino acids.

Buffers

Phosphate buffer, formate or acetate buffer, AMP buffer, calcium tartrate, glycine buffer, phosphate citrate buffer, tris buffer, ECT.

If it is desired a formulation may employ such a composition including beneficial microorganisms. The compounds thus defined may be applied to the plants by conventional methods including seed application techniques.

What is claimed is:

1. A method of improving crop yield comprising the application of a composition comprising the antiauxin 4-phenylbutyric acid to plants or soil.

2. A method of improving crop yield comprising the application of a composition comprising the antiauxin 4-phenylbutyric acid and an admix component to plants or soil.

3. A method for controlling auxin in plants by applying a composition comprising 4-PHENYLBUTYRIC acid to the said plant or the soil of said plant.

* * * * *